US00PP12054P2

(12) United States Plant Patent
Glicenstein

(10) Patent No.: US PP12,054 P2
(45) Date of Patent: Aug. 14, 2001

(54) AZALEA PLANT NAMED 'HONESTY'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/590,626

(22) Filed: Jun. 8, 2000

(51) Int. Cl.[7] ..... A01H 5/00
(52) U.S. Cl. ..... Plt./238
(58) Field of Search ..... Plt./238

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Azalea plant named 'Honesty', characterized by its dark green glossy leaves that do not abscise during the cooling and forcing periods; dense and outwardly spreading plant habit; freely branching habit; uniform flowering response; freely flowering habit; large, showy, double white-colored flowers; and excellent post-production longevity with plants maintaining good flower substance for more than four weeks in an interior environment.

1 Drawing Sheet

BACKGROUND OF THE INVENTION

The present Invention relates to a new and distinct cultivar of Azalea, botanically known as *Rhododendron hybrida*, an evergreen greenhouse-forcing type Azalea, and hereinafter referred to by the name 'Honesty'.

The new Azalea is a product of a planned breeding program conducted by the Inventor in Salinas, Calif. and Alva, Fla. The objective of the breeding program is to create new Azalea varieties having uniform plant habit, profuse and uniform flowering, dark green foliage, good foliage retention during the cooling and forcing periods, resistance to Cylindrocladium, and excellent postproduction longevity.

The new Azalea originated from a cross made by the Inventor in February, 1992, in Salinas, Calif., of the cultivar 'Cachet', disclosed in U.S. Plant Pat. No. 6,412, as the female, or seed, parent with the cultivar 'Alaska', not patented, as the male, or pollen, parent. The new Azalea was discovered and selected by the Inventor as a flowering plant within the progeny of the stated cross in a controlled environment in Alva, Fla., in June, 1994. The selection of this plant was based on its uniform plant habit, dark green foliage, double flower form, white flower color, large flower size, uniform flowering response, and excellent postproduction longevity.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Honesty'. These characteristics in combination distinguish 'Honesty' as a new and distinct cultivar:

1. Dark green glossy leaves that do not abscise during the cooling and forcing periods.
2. Dense and outwardly spreading plant habit.
3. Freely branching habit.
4. Uniform flowering response.
5. Freely flowering habit.
6. Large, showy, double white-colored flowers.
7. Excellent postproduction longevity with plants maintaining good flower substance for more than four weeks in an interior environment. Flowers typically do not shatter.
8. Very low incidence of infection with Cylindrocladium in inoculated trials.

Plants of the new Azalea differ from plants of the female parent, the cultivar 'Cachet', primarily in flower color as plants of the cultivar 'Cachet' have fuchsia pink-colored flowers.

Plants of the new Azalea differ from plants of the male parent, the cultivar 'Alaska', in the following characteristics:

1. Plants of the new Azalea are more compact than plants of the cultivar 'Alaska'.
2. Plants of the new Azalea have darker green, glossier and smaller leaves than plants of the cultivar 'Alaska'.
3. Flowers of plants of the new Azalea do not shatter whereas flowers of the cultivar 'Alaska' shatter.

Plants of the new Azalea can be compared to the plants of the cultivar 'Irish Lace', disclosed in U.S. Plant Pat. No. 11,187. However, in side-by-side comparisons conducted by the Inventor in Salinas, Calif., plants of the new Azalea differed from plants of the cultivar 'Irish Lace' in the following characteristics:

1. Plants of the new Azalea are more vigorous and have a more uniform plant habit than plants of the cultivar 'Irish Lace'.
2. When forced, plants of the new Azalea flower about ten days later than plants of the cultivar 'Irish Lace'.
3. The flower color of plants of the new Azalea is more white with less light green than the flower color of plants of the cultivar 'Irish Lace'.
4. Plants of the new Azalea last about eight days longer than plants of the cultivar 'Irish Lace' in postproduction longevity trials.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the actual colors of the new Azalea.

The photograph at the top of the sheet comprises a top perspective view of a typical plant of 'Honesty'.

The photograph at the bottom of the sheet is a close-up view of typical flowers of 'Honesty'.

DETAILED BOTANICAL DESCRIPTION

The aforementioned and following observations, measurements, values, and comparisons describe multiple plants grown in Salinas, Calif., in 12.5-cm containers in greenhouses during the spring under commercial production conditions. After flower bud development, plants were cooled at 3 to 5° C. for four weeks to break flower bud dormancy. Plants were subsequently forced into flower under commercial production conditions in a greenhouse. Plants described were about one year old.

In the following description, color references are made to The Royal Horticultural Society Colour Chart except where general terms of ordinary dictionary significance are used.

Botanical classification:

*Botanical.*—*Rhododendron hybrida* 'Honesty'.

*Commercial.*—Evergreen greenhouse-forcing type Azalea.

Parentage:

*Female or seed parent.*—*Rhododendron hybrida* cultivar 'Cachet', disclosed in U.S. Plant Pat. No. 6,412.

*Male or pollen parent.*—*Rhododendron hybrida* cultivar 'Alaska', not patented.

Propagation:

*Type.*—By terminal vegetative cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; outwardly spreading plant habit; inverted triangle; vigorous growth habit. Densely foliated. Freely flowering; numerous flowers per plant.

*Branching habit.*—Freely branching; about three or four lateral branches develop after removal of terminal apex.

*Plant height, soil level to top of flowers.*—About 30.5 cm.

*Plant diameter, area of spread.*—About 45 cm.

*Lateral branch description.*—Length: About 21 cm. Diameter at base: About 6 mm. Texture: Pubescent; fine golden brown hairs. Color: Immature: 146C to 146D. Mature: Woody, between 164A and 165A.

Foliage description:

*Arrangement.*—Alternate, single.

*Length.*—About 4.3 cm.

*Width.*—About 2.1 cm.

*Shape.*—Elliptic.

*Apex.*—Cuspidate.

*Base.*—Cuneate.

*Margin.*—Entire.

*Texture.*—Leathery, tough; durable; pubescent.

*Color.*—Young foliage, upper surface: Glossy; slightly darker than 147A. Young foliage, lower surface: Close to 147B. Mature foliage, upper surface: Glossy; darker than 147A. Mature foliage, lower surface: Close to 147B.

*Petiole.*—Length: About 6 mm. Diameter: About 2 mm. Color: Close to 147B.

Flower description:

*Natural flowering season.*—Spring after sufficient cool period. If forced, plants typically flower about 34 days after a four-week cooling treatment.

*Flower arrangement.*—Flowers arranged singly at terminals with usually about three to five flowers per apex. Flowers face upward and outward. Freely flowering. Not fragrant.

*Flower appearance.*—Large double flower form; stamens typically petaloid; sepals partially transformed into petal-like structures. Under less favorable environmental conditions, flowers may be semi-double or even single in form. White-colored petals tinged with light green at the base when developing. Flowers persistent.

*Flower diameter.*—About 8.5 cm.

*Flower depth.*—About 4.6 cm.

*Postproduction longevity.*—Under interior conditions, plants maintain good flower substance for more than four weeks.

*Flower bud* (*just starting to show petal color*).—Rate of opening: About three to four days depending on temperatures. Length: About 1.5 cm. Diameter: About 1 cm. Shape: Ovoid. Color: 144A to 144B.

*Petals.*—Arrangement: Double flower form; single whorl of five fused petals surrounding stamens that are typically transformed into petaloids. Length: About 5.7 cm. Width: About 4.1 cm. Shape: Roughly spatulate with mostly rounded apex. Margin: Entire; undulating. Texture: Smooth, satiny. Color: When opening, upper surface: White, 155D, with light green, 145C to 145D, at base. When opening, lower surface: White, 155D, with green, 144B to 144C, spots towards base; light greenish tinge, 145C to 145D, at base. Fully opened, upper surface: Mostly white, 155D, with green, 144B to 144C, spots at base of three uppermost petals; iridescent. Fully opened, lower surface: Mostly white, 155D, with faint green, 145C to 145D, towards base.

*Petaloids.*—Quantity: Typically about five or six. Appearance: Similar in color to petals, but smaller and irregular in size and shape. Length: About 4.1 cm. Width: About 2.2 cm. Shape: Irregular. Margin: Mostly entire; undulating. Texture: Smooth, satiny. Color: Fully opened, upper surface: Mostly white, 155D, with green, 144B to 144C, spots at base of three uppermost petaloids; iridescent. Fully opened, lower surface: Mostly white, 155D, with faint green, 145C to 145D, towards base.

*Sepals.*—Arrangement: Single whorl of five sepals, fused; partially transformed into petal-like structures. Varying in shape and size. Shape: Lanceolate with sharply acute apex. Margin: Entire. Texture: Pubescent on lower surface and at margin. Color, upper and lower surface: Mostly white, 155D, with green, close to 143A, longitudinal stripes, spots and margins.

*Peduncles.*—Length: About 1.6 cm. Diameter: About 2 mm. Angle: Upright. Strength: Flexible; strong. Texture: Very pubescent. Color: Base, 144A, towards apex, 144B.

*Reproductive organs.*—Androecium: Stamens: Typically transformed into petaloids. Gynoecium: Pistil quantity: One. Pistil length: About 2.4 cm. Stigma shape: Rounded. Stigma color: Initially green, 144A to 144B to 144C to 144D, eventually white, 155D. Style length: About 2.1 mm. Style color: Initially green, 144A to 144B to 144C to 144D, eventually white, 155D. Ovary color: 144A; heavily whiskered.

*Seed.*—Seed production has not been observed.

Disease resistance: In inoculated trials that were conducted in Alva, Fla. during the summers of 1997 and 1999, a very low incidence of infection by Cylindrocladium was observed.

It is claimed:

1. A new and distinct Azalea plant named 'Honesty', as illustrated and described.

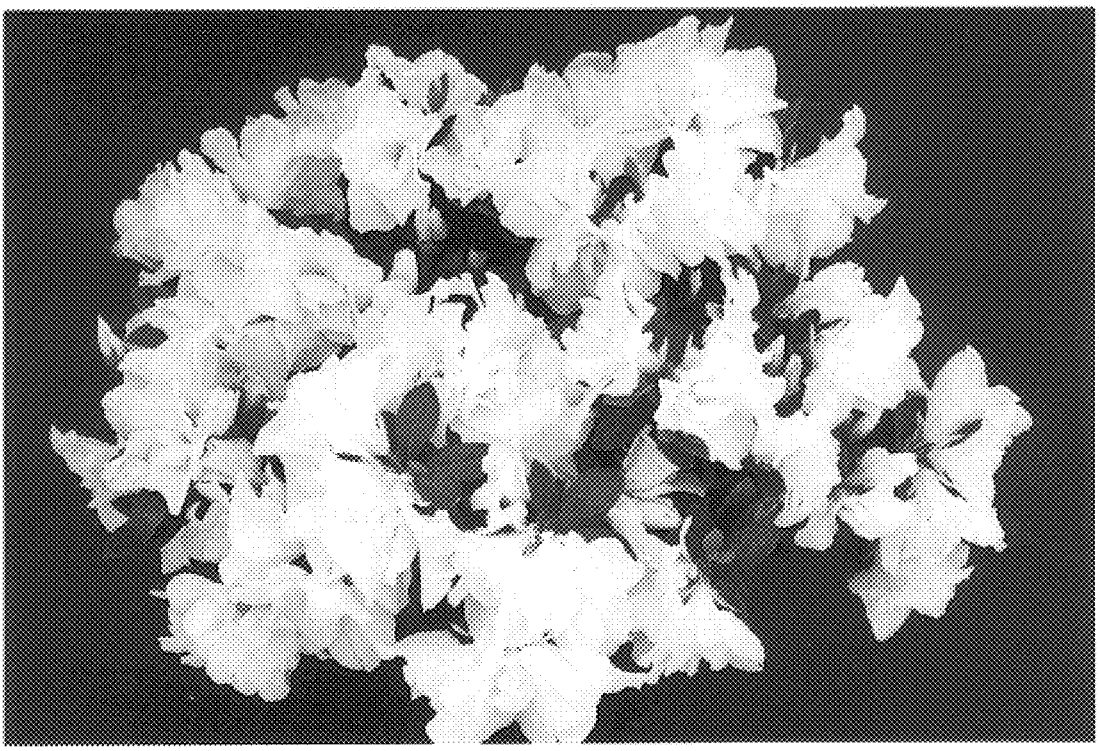
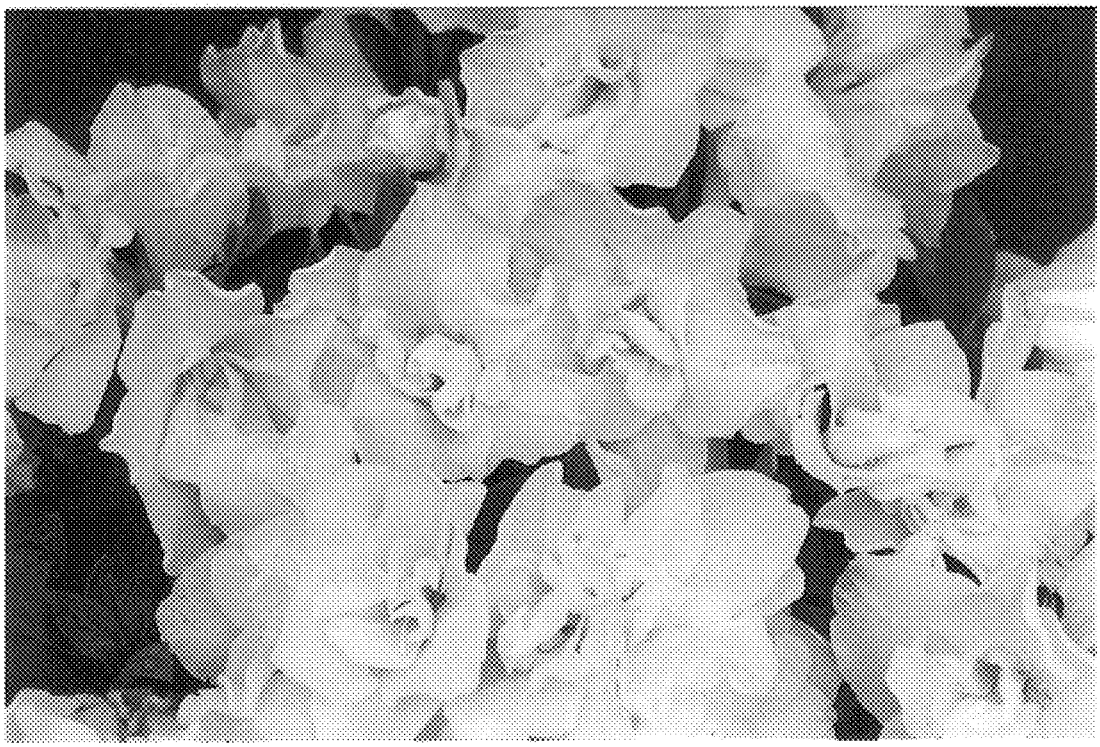

* * * * *